(12) United States Patent
Prakash et al.

(10) Patent No.: US 8,728,067 B2
(45) Date of Patent: May 20, 2014

(54) MICROWAVE ANTENNA PROBE HAVING A DEPLOYABLE GROUND PLANE

(75) Inventors: Mani N. Prakash, Boulder, CO (US); Francesca Rossetto, Longmont, CO (US); Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 1108 days.

(21) Appl. No.: 12/719,657

(22) Filed: Mar. 8, 2010

(65) Prior Publication Data

US 2011/0218527 A1    Sep. 8, 2011

(51) Int. Cl.
*A61B 18/18* (2006.01)

(52) U.S. Cl.
USPC .............................. 606/33; 606/41

(58) Field of Classification Search
USPC ...................................... 606/32–45
See application file for complete search history.

(56) References Cited

U.S. PATENT DOCUMENTS

| | | |
|---|---|---|
| 3,534,752 A | 10/1970 | Vanzini |
| D263,020 S | 2/1982 | Rau, III |
| D295,893 S | 5/1988 | Sharkany et al. |
| D295,894 S | 5/1988 | Sharkany et al. |
| 5,117,828 A | 6/1992 | Metzger et al. |
| 5,472,441 A | 12/1995 | Edwards et al. |
| 5,941,896 A | 8/1999 | Kerr |
| 6,051,014 A | 4/2000 | Jang |
| D424,694 S | 5/2000 | Tetzlaff et al. |
| D425,201 S | 5/2000 | Tetzlaff et al. |
| 6,067,475 A | 5/2000 | Graves et al. |
| 6,179,832 B1 | 1/2001 | Jones et al. |
| 6,245,088 B1 | 6/2001 | Lowery |
| D449,886 S | 10/2001 | Tetzlaff et al. |
| 6,364,896 B1 | 4/2002 | Addis |
| D457,958 S | 5/2002 | Dycus et al. |
| D457,959 S | 5/2002 | Tetzlaff et al. |
| 6,432,122 B1 | 8/2002 | Gilson et al. |
| 6,463,332 B1 | 10/2002 | Aldrich |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

International Search Report EP11001872 dated Jul. 6, 2011.

(Continued)

*Primary Examiner* — Linda Dvorak
*Assistant Examiner* — Amanda Scott

(57) ABSTRACT

A surgical ablation system employing an ablation probe having a deployable ground plane is disclosed. The disclosed system includes a source of ablation energy and a source of electrosurgical energy, and a switching assembly configured to select between ablation and electrosurgical modes. The probe includes a cannula having a shaft slidably disposed therein. The shaft includes a deployable ground plane electrode assembly and a needle electrode disposed at distal end of the shaft. As the shaft is extended distally from the cannula, the ground plane electrode unfolds, and the needle electrode is exposed. Electrosurgical energy is applied to tissue via the needle electrode to facilitate the insertion thereof into tissue. Ablation energy is applied to tissue via the needle electrode to achieve the desired surgical outcome. The shaft, ground plane electrode and needle electrode are retracted into the cannula, and withdrawn from the surgical site.

20 Claims, 11 Drawing Sheets

(56) References Cited

U.S. PATENT DOCUMENTS

| | | |
|---|---|---|
| 6,485,486 B1 | 11/2002 | Trembly et al. |
| 6,503,247 B2 | 1/2003 | Swartz et al. |
| 6,551,341 B2 | 4/2003 | Boylan et al. |
| 6,603,994 B2 | 8/2003 | Wallace et al. |
| 6,638,277 B2 | 10/2003 | Schaefer et al. |
| 6,638,294 B1 | 10/2003 | Palmer |
| 6,669,693 B2 | 12/2003 | Friedman |
| 6,682,526 B1 | 1/2004 | Jones et al. |
| 6,689,126 B1 | 2/2004 | Farley et al. |
| 6,692,490 B1 | 2/2004 | Edwards |
| D496,997 S | 10/2004 | Dycus et al. |
| D499,181 S | 11/2004 | Dycus et al. |
| 6,881,213 B2 | 4/2005 | Ryan et al. |
| 6,893,431 B2 | 5/2005 | Naimark et al. |
| 6,939,348 B2 | 9/2005 | Malecki et al. |
| 7,003,342 B2 | 2/2006 | Plaza |
| 7,025,767 B2 | 4/2006 | Schaefer et al. |
| 7,041,098 B2 | 5/2006 | Farley et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| 7,186,251 B2 | 3/2007 | Malecki et al. |
| D541,418 S | 4/2007 | Schechter et al. |
| D541,938 S | 5/2007 | Kerr et al |
| 7,293,562 B2 | 11/2007 | Malecki et al. |
| 7,306,595 B2 | 12/2007 | Ostrovsky et al. |
| D564,662 S | 3/2008 | Moses et al. |
| 7,367,975 B2 | 5/2008 | Malecki et al. |
| 7,410,485 B1 | 8/2008 | Fink et al. |
| 7,455,670 B2 | 11/2008 | Laufer |
| D613,412 S | 4/2010 | DeCarlo |
| 2002/0156472 A1 | 10/2002 | Lee et al. |
| 2004/0162555 A1 | 8/2004 | Farley et al. |
| 2004/0254621 A1 | 12/2004 | Jones et al. |
| 2005/0228370 A1 | 10/2005 | Sterzer et al. |
| 2005/0251200 A1 | 11/2005 | Porter |
| 2006/0106375 A1 | 5/2006 | Werneth et al. |
| 2007/0203480 A1* | 8/2007 | Mody et al. ............ 606/33 |
| 2007/0219546 A1 | 9/2007 | Mody et al. |
| 2007/0287999 A1 | 12/2007 | Malecki et al. |
| 2007/0299434 A1 | 12/2007 | Malecki et al. |
| 2008/0009747 A1 | 1/2008 | Saadat et al. |
| 2008/0255553 A1* | 10/2008 | Young et al. ............ 606/33 |
| 2010/0049178 A1* | 2/2010 | Deem et al. ............ 606/9 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 1186274 | 3/2002 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO95/05869 | 3/1995 |
| WO | WO99/04704 | 2/1999 |
| WO | WO 2008131302 | 10/2008 |
| WO | WO2010/035831 | 4/2010 |

OTHER PUBLICATIONS

U.S. Appl. No. 08/483,742, filed Jun. 7, 1995.
U.S. Appl. No. 08/136,098, filed Oct. 14, 1993.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/423,609, filed Apr. 14, 2009.
U.S. Appl. No. 12/436,231, filed May 6, 2009.
U.S. Appl. No. 12/436,237, filed May 6, 2009.
U.S. Appl. No. 12/436,239, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.

(56) References Cited

OTHER PUBLICATIONS

U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/556,238, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,323, filed Nov. 16, 2009.
U.S. Appl. No. 12/619,462, filed Nov. 16, 2009.
U.S. Appl. No. 12/620,289, filed Nov. 17, 2009.
U.S. Appl. No. 12/642,623, filed Dec. 18, 2009.
U.S. Appl. No. 12/686,726, filed Jan. 13, 2010.
U.S. Appl. No. 12/692,856, filed Jan. 25, 2010.
U.S. Appl. No. 12/696,671, filed Jan. 29, 2010.
U.S. Appl. No. 12/696,966, filed Jan. 29, 2010.
U.S. Appl. No. 12/701,030, filed Feb. 5, 2010.
U.S. Appl. No. 12/708,974, filed Feb. 19, 2010.
U.S. Appl. No. 12/709,014, filed Feb. 19, 2010.
U.S. Appl. No. 12/712,864, filed Feb. 25, 2010.
U.S. Appl. No. 12/713,429, filed Feb. 26, 2010.
U.S. Appl. No. 12/713,515, filed Feb. 26, 2010.
U.S. Appl. No. 12/713,641, filed Feb. 26, 2010.
U.S. Appl. No. 12/722,034, filed Mar. 11, 2010.
U.S. Appl. No. 12/731,367, filed Mar. 25, 2010.
U.S. Appl. No. 12/732,508, filed Mar. 26, 2010.
U.S. Appl. No. 12/732,521, filed Mar. 26, 2010.
U.S. Appl. No. 12/761,267, filed Apr. 15, 2010.
U.S. Appl. No. 12/769,457, filed Apr. 28, 2010.
U.S. Appl. No. 12/772,675, filed May 3, 2010.
U.S. Appl. No. 12/777,984, filed May 11, 2010.
U.S. Appl. No. 12/786,671, filed May 25, 2010.
U.S. Appl. No. 12/787,639, filed May 26, 2010.
U.S. Appl. No. 12/792,904, filed Jun. 3, 2010.
U.S. Appl. No. 12/792,932, filed Jun. 3, 2010.
U.S. Appl. No. 12/792,947, filed Jun. 3, 2010.
U.S. Appl. No. 12/792,970, filed Jun. 3, 2010.
U.S. Appl. No. 12/793,037, filed Jun. 3, 2010.
U.S. Appl. No. 12/819,330, filed Jun. 21, 2010.
U.S. Appl. No. 12/823,211, filed Jun. 25, 2010.
U.S. Appl. No. 12/826,902, filed Jun. 30, 2010.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.

Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one p. Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advancedinput.com/lightkey> last visited on Feb. 10, 2005.

(56) References Cited

OTHER PUBLICATIONS

Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, " LigaSure™ System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . ." Journal of Applied Sciences. Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.

(56) References Cited

OTHER PUBLICATIONS

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report Ep 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.

(56) References Cited

OTHER PUBLICATIONS

European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

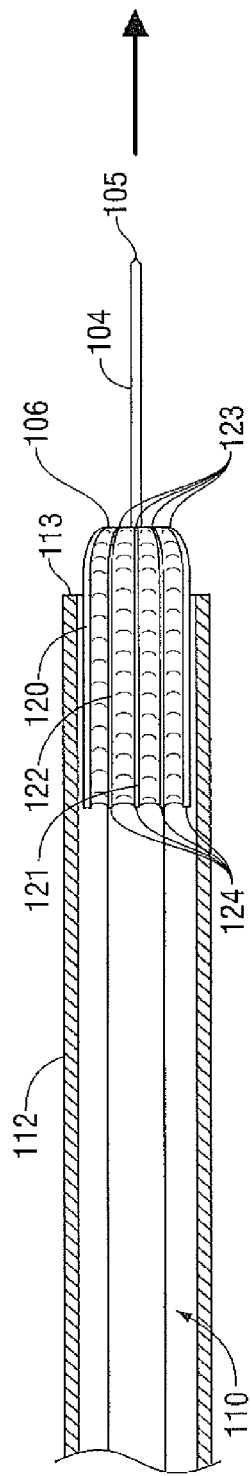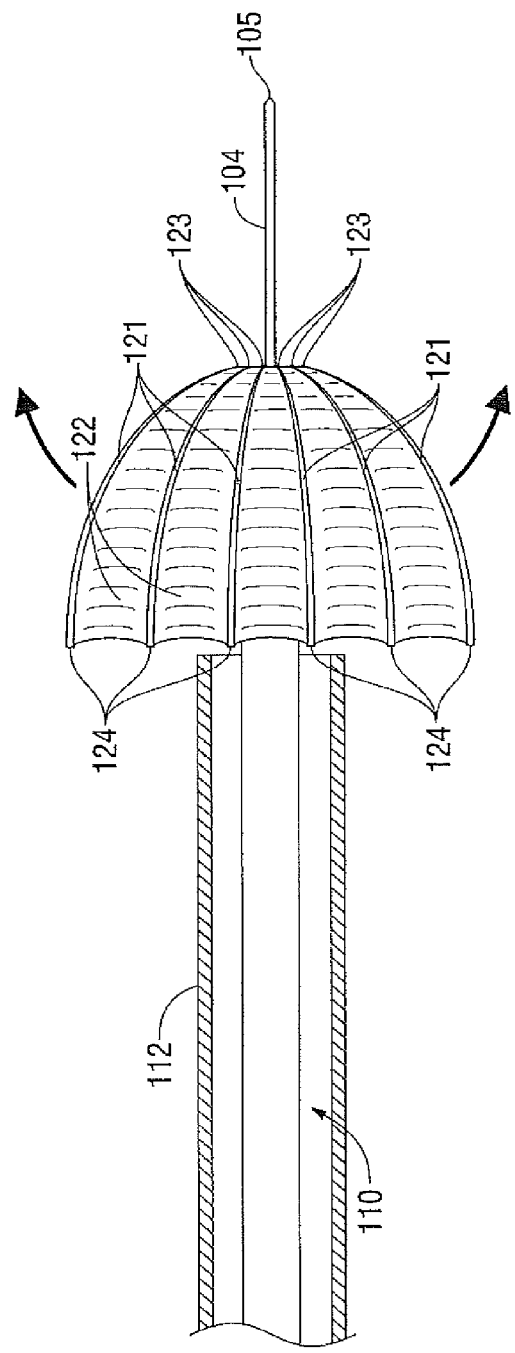

MICROWAVE ANTENNA PROBE HAVING A DEPLOYABLE GROUND PLANE

BACKGROUND

1. Technical Field

The present disclosure relates to systems and methods for providing energy to biological tissue and, more particularly, to a microwave ablation surgical system and probe having a deployable ground plane, and methods of use therefor.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery is a technique of using alternating current electrical signals, using a carrier frequency in the approximately 200 kHz-3.3 MHz range, in connection with surgical instruments, to cut or coagulate biologic tissue endogenically. This electrosurgical signal can be a sinusoidal waveform operating in a continuous mode at a 100% duty cycle, or pulse modulated at a duty cycle of less than 100%. Typically, electrosurgical signals are operated at 100% duty cycle for maximal cutting effect, and are pulse modulated at duty cycles ranging from 50% to 25% for less aggressive cutting, also referred to as blending, or, at a substantially lower duty cycle of approximately 6%, for coagulating. The electrosurgical carrier signal can also be varied in intensity. The electrosurgical signal is applied to the patient via electrodes in either monopolar mode, or bipolar mode. In monopolar mode, the active electrode is the surgical instrument at the surgical site, and the return electrode is elsewhere on the patient, such that the electrosurgical signal passes through the patient's body from the surgical site to the return electrode. In bipolar mode, both the active and return electrodes are at the surgical site, effectuated by, for example, both jaw members of a pair of forceps, such that the electrosurgical signal passes through only the tissue that is held between the jaw members of the instrument.

In tissue ablation electrosurgery, electrosurgical energy (e.g., microwave, radiofrequency) may be delivered to targeted tissue by an antenna or probe. There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis. The tuning of a helical antenna assembly may be determined, at least in part, by the physical characteristics of the helical antenna element, e.g., the helix diameter, the pitch or distance between coils of the helix, and the position of the helix in relation to the probe assembly to which it is mounted.

The typical microwave antenna has a long, thin inner conductor that extends along the longitudinal axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 300 MHz to about 10 GHz is applied to a targeted tissue site to create an ablation volume, which may have a particular size and shape. Ablation volume is correlated to antenna design, antenna performance, antenna impedance and tissue impedance. The particular type of tissue ablation procedure may dictate a particular ablation volume in order to achieve a desired surgical outcome. By way of example, and without limitation, a spinal ablation procedure may call for a longer, narrower ablation volume, whereas in a prostate or liver ablation procedure, a more spherical ablation volume may be required.

In some instances, targeted lesions may be located on or near the surface of the target organ, e.g., the "dome" or top of a liver. Conventional ablation probes may radiate ablation energy into the surrounding tissue, for example, the abdominal wall. In such instances, surface lesions may treated with an invasive ablation needle having a radial ground plane that is adapted to shield adjacent tissues from undesirable exposure to ablation energy. However, such ground planes may have a diameter that is substantially greater than that of the probe shaft, which may preclude the use of laparoscopic treatment, or, require a large puncture to be created in the skin and/or adjacent anatomical structures during such non-invasive procedures. Additionally, insertion of a needle probe into dense or fibrous tissue may be difficult and place stress on the probe, which may lead to probe failure and operative complications.

SUMMARY

The present disclosure is directed to a microwave ablation probe having a deployable ground plane electrode. The disclosed microwave ablation probe includes a shaft having an inner conductor and a dielectric coaxially disposed around the inner conductor. The inner conductor extends distally beyond a distal end of the dielectric to form a needle electrode. An outer shield is coaxially disposed around the dielectric and is coupled to a deployable ground plane assembly electromechanically joined to a distal end of the dielectric.

The ground plane assembly, as well as other ground plane assemblies described herein, may, when deployed, have a generally umbrella-like shape, however, it is to be understood the disclosed deployable ground planes may include any shape, including without limitation ovoid, polygonal, and a ground plane described by radial projections.

A ground plane assembly in accordance with the present disclosure may include one or more support wires extending radially from a distal end of the dielectric and/or the outer conductor. The support wires may be formed from resilient material, such as without limitation, spring steel, shape memory alloy, carbon fiber, fiberglass composite material, and the like. The support wires are arranged in a radial cantilever configuration, such that, in an embodiment, the wires extend approximately transversely to a longitudinal axis of the shaft when at rest (e.g., when the wires are in a deployed, unloaded or undeflected state).

A generally circular flexible conductive membrane is electromechanically fixed to the support wires in a generally umbrella-like fashion to form a ground plane electrode. Prior to use, the ground plane electrode may folded against the probe shaft, e.g., positioned in a stowed or undeployed configuration. The probe may be introduced into a cannula, which may have an inner diameter dimensioned to retain the folded ground plane electrode in the stowed configuration. During use, a distal end of a cannula having a described probe positioned therein, may be introduced to the surgical site. The cannula may be withdrawn and/or the probe may be advanced, causing the ground plane assembly to extend from the cannula to expose the ground plane assembly. Once free of the cannula, the biasing force of the wires causes the ground plane assembly to deploy, e.g., to fold open. The needle electrode may then be inserted into targeted tissue and a source of ablation energy activated to deliver ablation energy to targeted tissue. Electrosurgical energy (having, e.g., a cutting waveform) may be applied to tissue via the needle electrode to ease or facilitate the insertion of the needle electrode into tissue. After the needle electrode is positioned in tissue, ablation energy may then be applied to tissue to perform the desire ablation procedure.

Also disclosed is an electromagnetic surgical ablation system that includes a source of ablation energy and a source of electrosurgical energy, and a switching assembly configured to selectively apply either the source of ablation energy or the source of electrosurgical energy to an inner conductor of an ablation probe. The disclosed system includes an ablation probe comprising a generally tubular cannula having a proximal end and a distal end, and a shaft slidably disposed within the cannula and having at least a stowed position and a deployed position. The shaft includes an inner conductor adapted to operably couple to the switching assembly. The inner conductor may be coaxially disposed within the shaft, and may extend from a distal end thereof to form a needle electrode. The probe includes a deployable ground plane electrode assembly disposed about a distal end of the shaft, wherein, when the shaft is in a stowed position the deployable ground plane electrode is substantially folded within the cannula, and when the shaft is in a deployed position the deployable ground plane electrode extends substantially radially from a distal end of the shaft.

A method of using a surgical ablation system is presented herein, comprising the steps of positioning an ablation probe at an operative site, wherein the ablation probe includes a cannula having therein a deployable ground plane antenna and a distal needle electrode. The ground plane antenna and distal needle electrode are deployed (e.g., extended from the cannula). Electrosurgical energy may be delivered to tissue via the needle electrode to facilitate the insertion of the needle electrode into tissue, and the needle electrode is inserted into tissue. After the needle is inserted into tissue, ablation energy may be delivered to tissue via the needle electrode. After the ablation is complete, the needle electrode is withdrawn from tissue, the ground plane antenna is retracted into the cannula, and the ablation probe is removed from the operative site. The disclosed method may additionally include the step of insufflating the operative site with a gas, such as carbon dioxide, to form a pneumoperitoneum.

BRIEF DESCRIPTION OF THE DRAWINGS

The above and other aspects, features, and advantages of the present disclosure will become more apparent in light of the following detailed description when taken in conjunction with the accompanying drawings in which:

FIG. 4 is a side, partial cutaway view of an embodiment of a microwave ablation probe having a deployable ground plane, in a second position, in accordance with the present disclosure;

FIG. 5 is a side, partial cutaway view of an embodiment of a microwave ablation probe having a deployable ground plane, in a third position, in accordance with the present disclosure;

DETAILED DESCRIPTION

Particular embodiments of the present disclosure are described hereinbelow with reference to the accompanying drawings; however, it is to be understood that the disclosed embodiments are merely exemplary of the disclosure, which may be embodied in various forms. Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In addition, as used herein, the term "proximal" shall refer to the end of the instrument that is closer to the user, while the term "distal" shall refer to the end that is farther from the user, as is customary.

Figure 1:
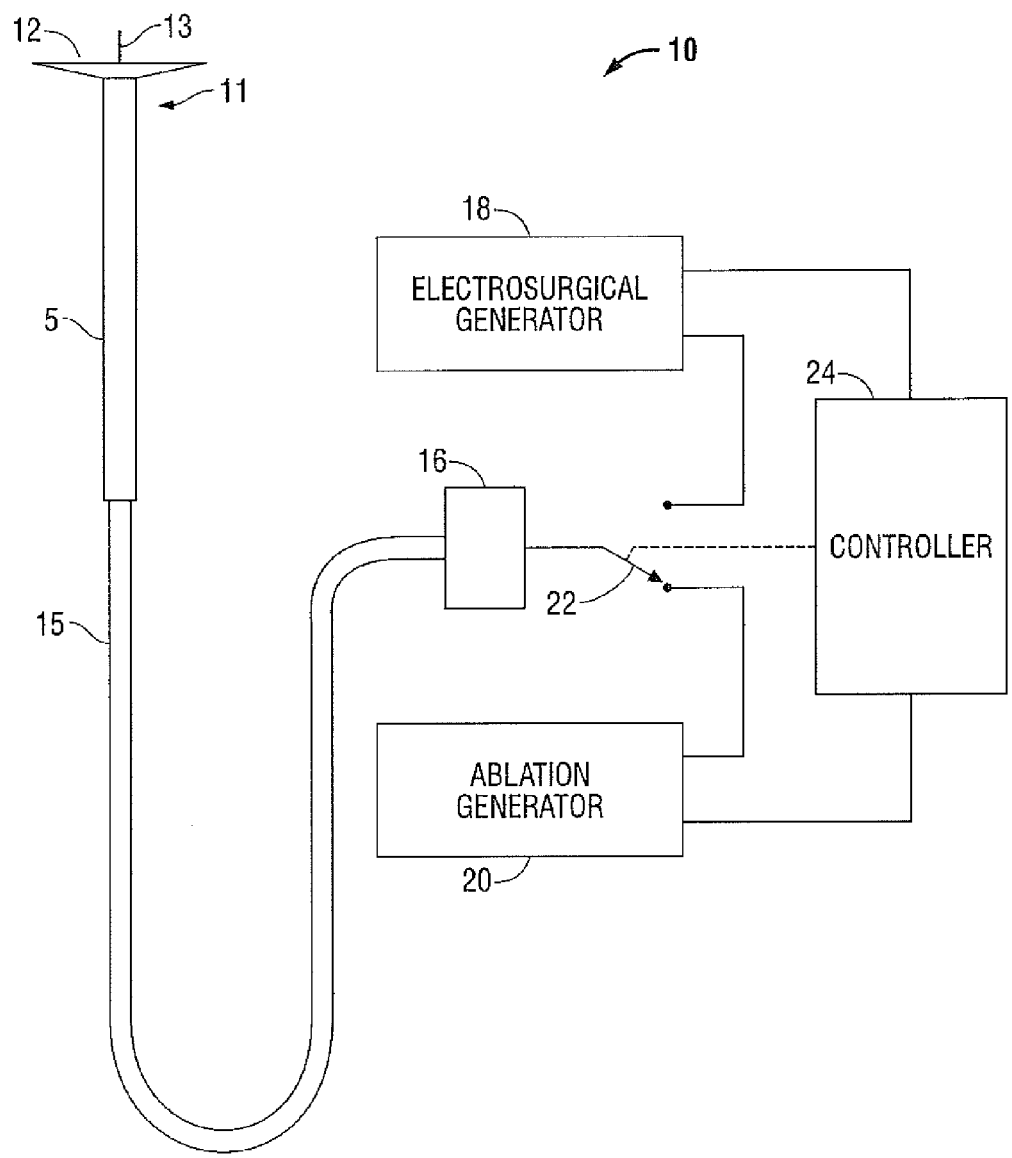
FIG. 1 is a schematic representation of a microwave ablation system that includes an ablation probe having a deployable ground plane in accordance with the present disclosure.

FIG. 1 shows an embodiment of a microwave ablation system 10 in accordance with the present disclosure. The microwave ablation system 10 includes an electromagnetic surgical ablation probe 5 operatively coupled by a cable 15 to connector 16, which may further operably couple the antenna probe 10 to a selector switch 22, which, in turn, selectively and operably couples an ablation generator assembly 20 and/or an electrosurgical generator assembly 18 to probe 10. Switch 22 may be any suitable switching device, including without limitation a mechanical switch, relay, semiconductor, and/or combinations thereof. Ablation generator 20, electrosurgical generator 18, and/or switch 22 may be operably coupled to a controller 24. Probe 10 includes a distal radiating portion 11 having a generally shallow umbrella-shaped ground plane 12 disposed thereupon. As depicted in FIG. 1, ground plane 12 is in a deployed position. A needle electrode 13 extends distally from the probe 10, which is also depicted in FIG. 1 in a deployed position. Ablation generator assembly 20 is a source of ablation energy, e.g., microwave or RF energy in a range of about 300 MHz to about 10 GHz. In embodiments, generator assembly 20 may provide ablation energy in a range of about 915 MHz to about 2.45 GHz. Electrosurgical generator 18 is a source of electrosurgical energy in a range of about 200 kHz to 3.3 MHz range and configured to provide one or more electrosurgical waveforms adapted to facilitate cutting, coagulating, blending, etc. Electrosurgical generator 18 may include a return electrode input (not explicitly shown) to accommodate a return electrode pad that is used during monopolar electrosurgical procedures.

Figure 2:
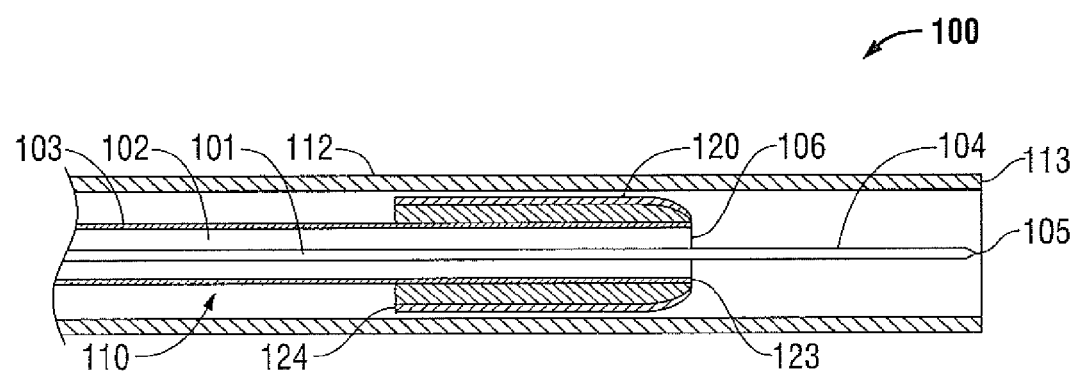
FIG. 2 is a side, cutaway view of an embodiment of a microwave ablation probe having a deployable ground plane in accordance with the present disclosure
Figure 3:
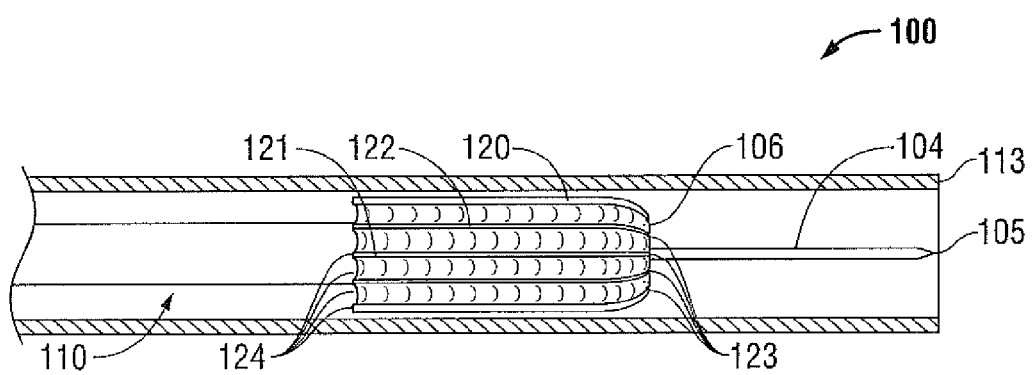
FIG. 3 is a side, partial cutaway view of an embodiment of a microwave ablation probe having a deployable ground plane, in a first position, in accordance with the present disclosure.

With reference to FIGS. 2 and 3, a coaxial fed microwave ablation probe 100 is shown. The disclosed probe 100 includes a shaft assembly 110 slidably disposed within a cannula 112. The shaft 110 includes an inner conductor 101 disposed coaxially within dielectric 102, and an outer conductor 103 coaxially disposed around the dielectric 102. The inner conductor 101 extends distally from the dielectric 102 to form a needle electrode 104, which may include a sharpened distal tip 105 to ease the insertion thereof into tissue. As shown in FIGS. 2 and 3, distal tip is substantially aligned with a distal end 113 of trocar 112.

Figure 6:
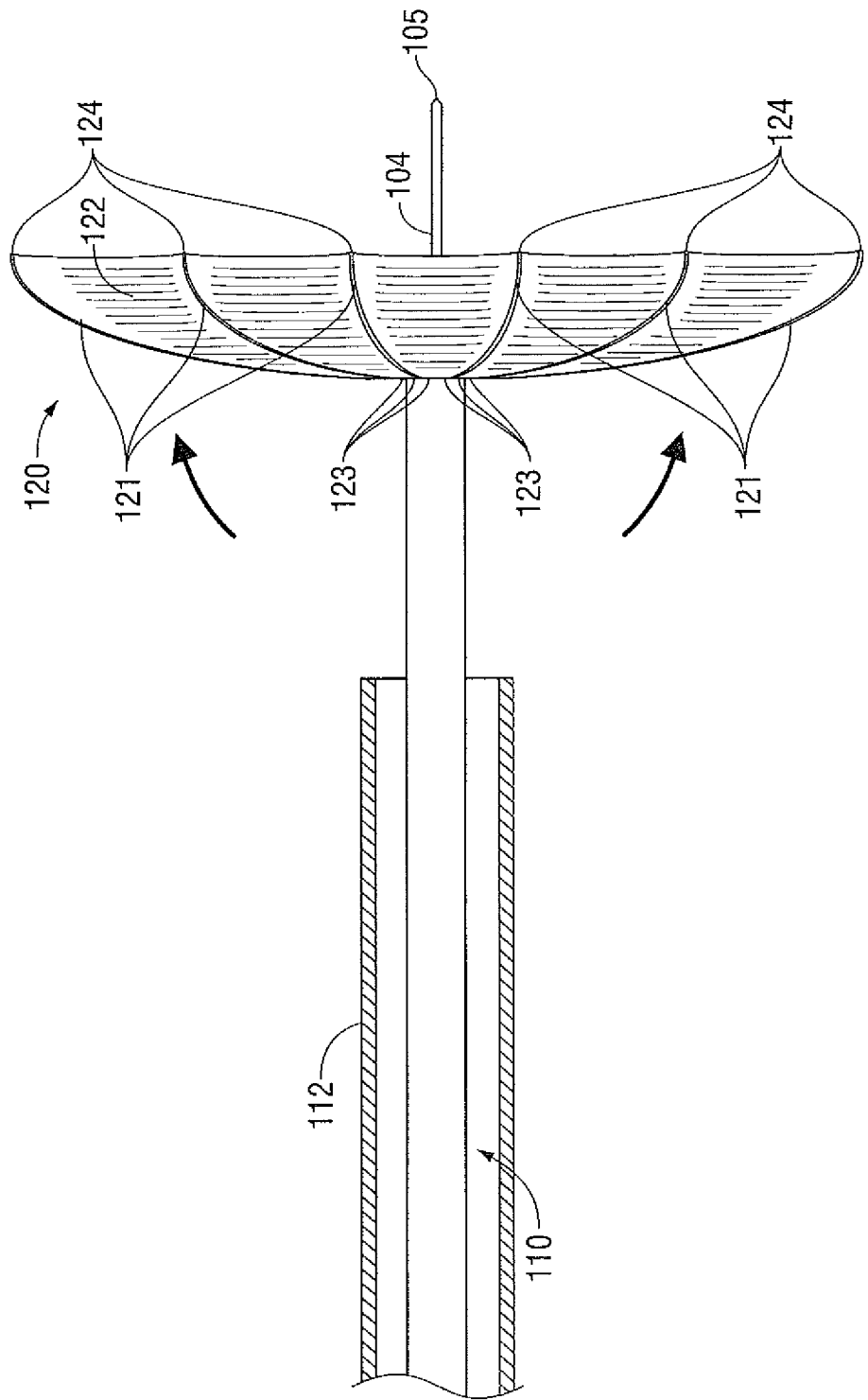
FIG. 6 is a side, partial cutaway view of an embodiment of a microwave ablation probe having a deployable ground plane, in a fourth position, in accordance with the present disclosure.

Shaft 110 includes an umbrella-like deployable ground plane electrode assembly 120 disposed generally at a distal end 106 of dielectric 102. The umbrella-like deployable ground plane assembly 120 includes a plurality of wire elements 121, each having a fixed end 123 and a free end 124. The umbrella-like deployable ground plane 120 assembly is movable between a stowed position, as seen generally in FIGS. 2 and 3, and a deployed position as seen in FIG. 6. The wire elements may be formed from any suitable resilient material having sufficient flexibility to be stowed in a first position while having sufficient elasticity to recover to a deployed position as shown in FIG. 6. For example, and without limitation, wire elements 121 may be formed from shape memory alloy (e.g., nitinol), stainless steel, platinum, or other material exhibiting similar elastic and recovery characteristics.

A fixed end 123 of each wire element 121 may be fixed to a distal end 106 of dielectric 102 such that, in a deployed position, a wire element 121 extends substantially radially from (orthogonal to) shaft 110. Fixed end 123 of wire element 121 may be joined to dielectric 102 by any suitable manner of connection, including without limitation by mechanical and/or interference fit into a corresponding opening (not explicitly shown) defined within dielectric 102, and/or by soldering, welding, brazing, adhesive coupling, and the like. Additionally or alternatively, a fixed end 123 of each wire element 121 may be fixed to a distal end of outer conductor 103 and operably electrically coupled thereto.

A flexible ground plane membrane 122 is disposed in electrical communication onto the plurality of wire elements 121 of umbrella-like deployable ground plane assembly 120. Ground plane membrane 122 may be formed from any electrically conductive material having sufficient flexibility, strength and heat resistance to enable the deployment and/or retrieval of ground plane assembly 120, such as, without limitation, metallic foil, metallic mesh, and/or metal-coated polymers, e.g., aluminized biaxially-oriented polyethylene terephthalate (a.k.a, boPET or Mylar™).

In a stowed or closed position, best illustrated in FIGS. 2 and 3, the ground plane assembly 120 is folded such that free ends 124 of wire elements 121 may be positioned substantially adjacent to or in contact with shaft 110 at a location proximal of a distal end of dielectric 102. An outward, or opening, bias of the wire elements 121 is resisted by the cannula 112 to confine ground plane assembly 120 to a stowed position. Ground plane assembly 120 may be moved to a deployed position as seen in FIGS. 4-6 by advancing the shaft 110 distally in relation to cannula 112, and/or, withdrawing cannula 112 proximally with respect to shaft 110.

Figure 7:
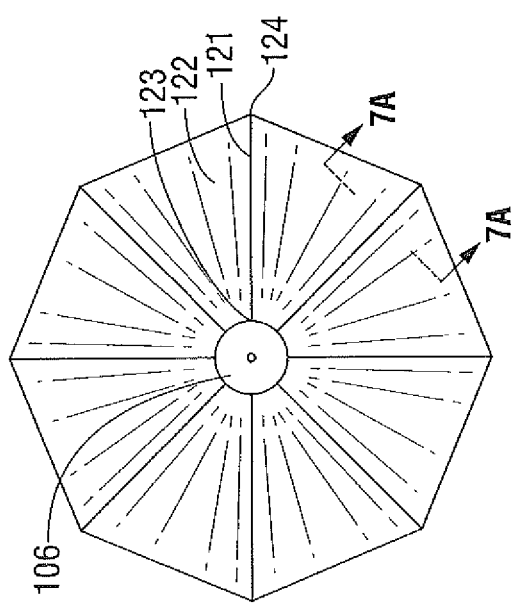
FIG. 7 is distal end view of an embodiment of a microwave ablation probe having a deployable ground plane in accordance with the present disclosure.

As seen in FIG. 4, shaft 110 has been moved distally with respect to cannula 112, thereby exposing a distal portion of ground plane assembly 120. An inner surface of cannula 112 may include a lubricious coating, such as without limitation, polytetrafluoroethylene (PTFE) (e.g., Teflon®, manufactured by E. I. du Pont de Nemours and Company of Wilmington, Del., United States), which may facilitate movement of shaft 110 and/or ground plane assembly 120 within cannula 112. As shown in FIG. 4, a proximal portion (e.g., the free ends 124) of closed ground plane assembly 120 remains within cannula 112, thereby retaining ground plane antenna 120 in a closed position. Turning now to FIG. 5, shaft 110 is moved further distally, moving ground plane assembly 120 clear of cannula 112 and thus enabling wire elements 121 to recover to a relaxed position, which causes ground plane 120 to open into a deployed position best seen in FIGS. 6 and 7. It is envisioned that the deployment of ground plane assembly 120 (once clear of cannula 112) may occur in a generally instantaneous motion or in a gradual motion. In embodiments, the deployment time of ground plane assembly 120 may range from less than 50 milliseconds to about five seconds.

Figure 7A:
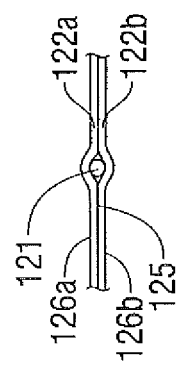
FIG. 7A is edge, cross sectional view of an embodiment of ground plane assembly in accordance with the present disclosure.

Ground plane assembly 120 may include a dielectric coating on a surface thereof, e.g., a distal surface, a proximal surface, or an edge thereof (as referenced to a ground plane assembly in an open or deployed position). Additionally or alternatively, ground plane membrane 122 may include a plurality of layers and/or laminations, as shown in FIG. 7A. In one envisioned embodiment, at least one inner surface 125 between layer 122a and 122b includes a metallic coating. An outer surface 126a and/or 126b includes a dielectric coating. It is also envisioned that a layer 122a and/or 122b may be formed from a dielectric material, such as without limitation PTFE, or boPET (e.g., Mylar®, manufactured by E. I. du Pont de Nemours and Company of Wilmington, Del., United States).

Figure 8:
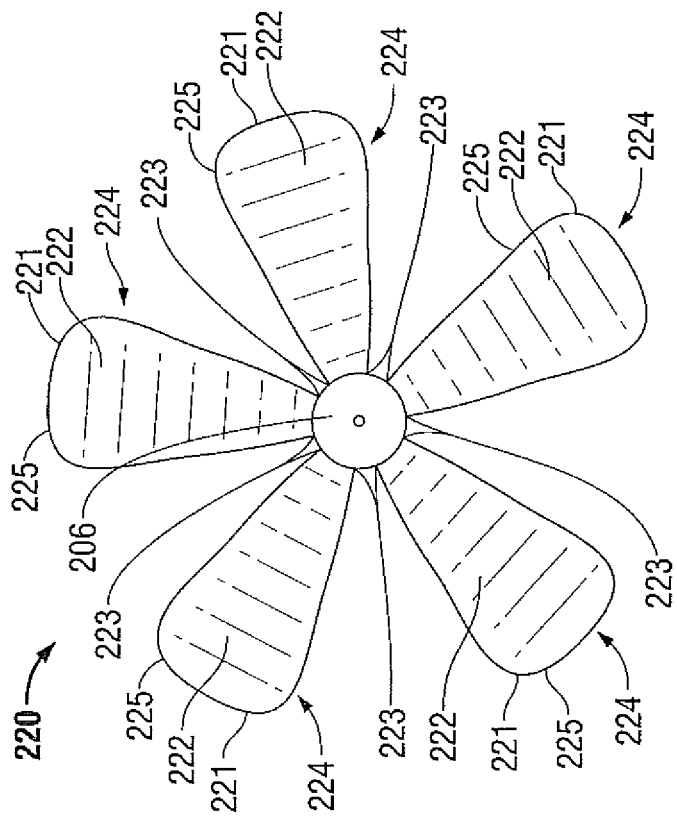
FIG. 8 is distal end view of another embodiment of a microwave ablation probe having a deployable ground plane in accordance with the present disclosure.

Additional envisioned embodiments of a ground plane assembly in accordance with the present disclosure are discussed with reference to FIGS. 8-11. As seen in FIG. 8, a ground plane assembly includes one or more leaf-like ground plane elements 224 radially disposed about a dielectric distal end 206. Each ground plane element 224 includes a wire element 221 having two fixed ends 223 that are operably fixed to a dielectric distal end 206 as described hereinabove to form a petal-like wire loop 225. A ground plane membrane 222 is disposed upon each wire loop 225 to form a ground plane element 224. Each ground plane element may be stowed within a cannula (not explicitly shown) in a closed position, and deployed at an operative site into an open position as described herein.

Figure 9:
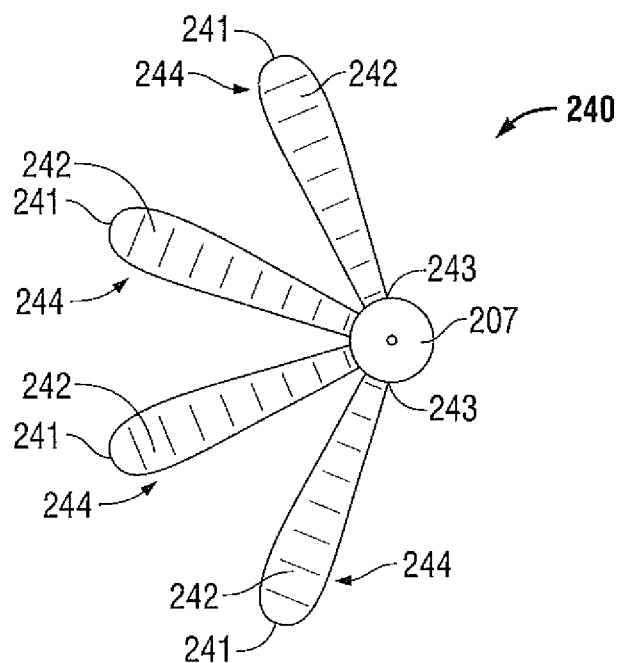
FIG. 9 is distal end view of yet another embodiment of a microwave ablation probe having a deployable ground plane in accordance with the present disclosure.

In FIG. 9, an alternative ground plane assembly 240 is depicted wherein one or more ground plane elements 224 are disposed in an asymmetrical radial arrangement. Such an asymmetrical arrangement may provide alternative ablation patterns which may be desirable in particular surgical scenarios, e.g., wherein irregularly-shaped or asymmetrical tumors or lesions are targeted. In an embodiment, wire element 241 may include a score (not explicitly shown) at a juncture 243 where wire element 241 is joined to dielectric distal end 207. A user (e.g., a surgeon) may tailor a ground plane assembly 240 by bending unwanted ground plane elements 244 at the score until the wire element 241 breaks, thus enabling the removal of individual ground plane elements 244 from the ground plane assembly 240. In this manner, the ablation pattern and/or physical dimensions of the ground plane assembly and probe associated therewith may be adapted to the particular requirements of a surgical procedure.

Figure 10:
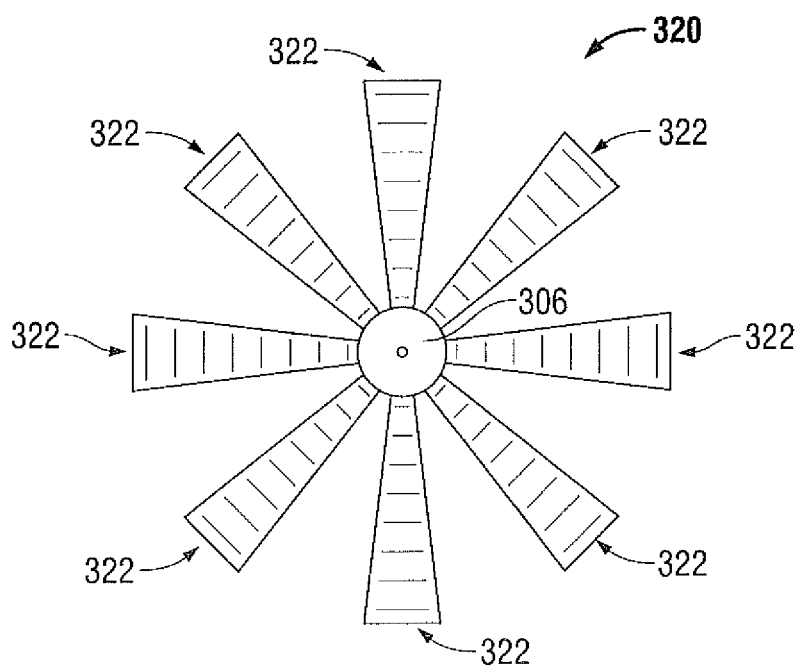
FIG. 10 is distal end view of still another embodiment of a microwave ablation probe having a deployable ground plane in accordance with the present disclosure.
Figure 10A:
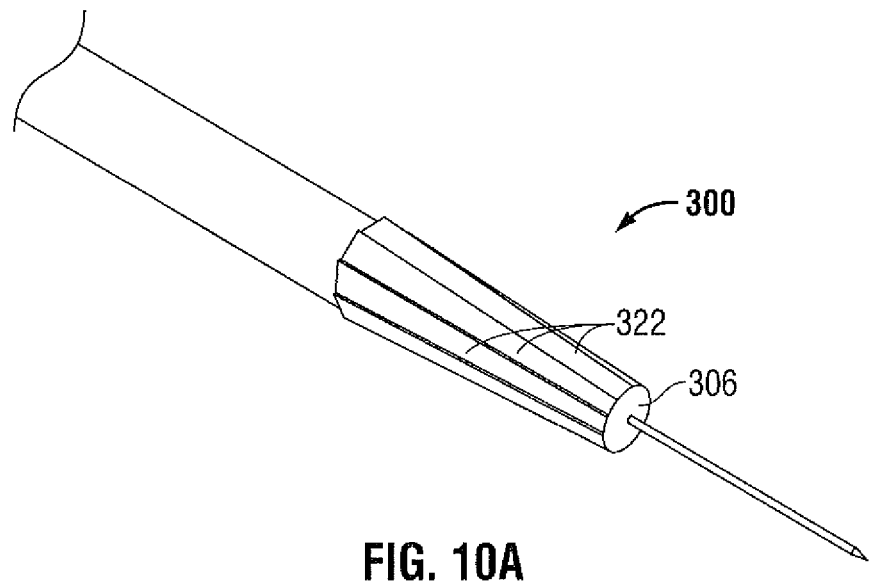
FIG. 10A is a perspective view of the FIG. 10 embodiment of a microwave ablation probe having a deployable ground plane assembly in a closed position, in accordance with the present disclosure.
Figure 10B:
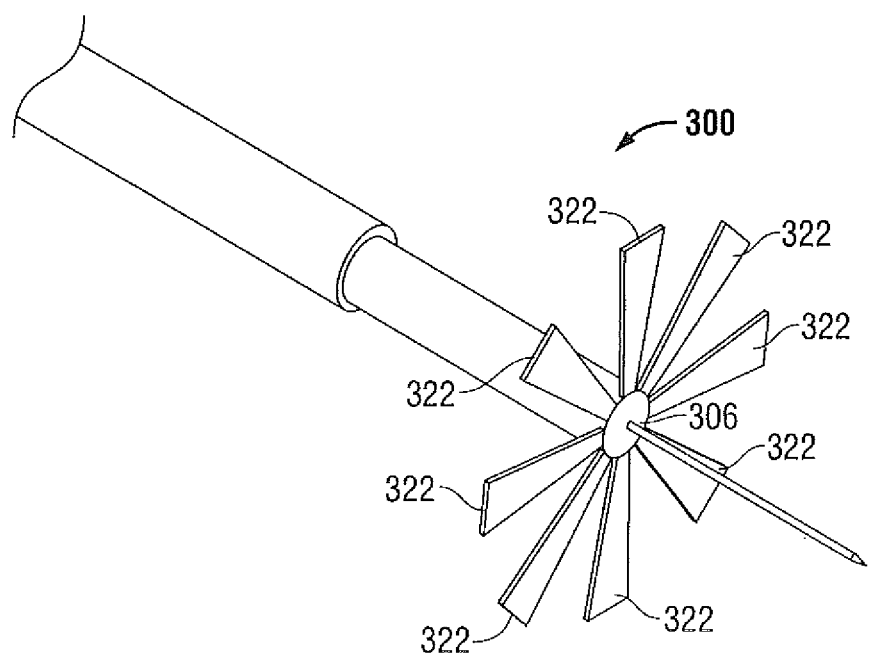
FIG. 10B is a perspective view of the FIG. 10 embodiment of a microwave ablation probe having a deployable ground plane assembly in an open position, in accordance with the present disclosure.
Figure 13A:
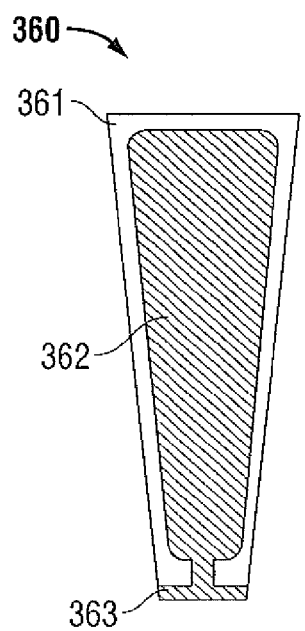
FIG. 13A illustrates an embodiment of a ground plane leaf having a conductive element disposed thereupon in accordance with the present disclosure.
Figure 13B:
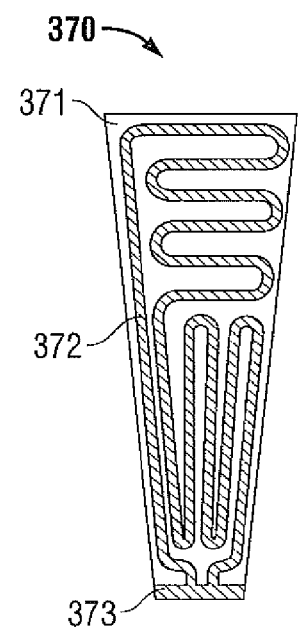
FIG. 13B illustrates another embodiment of a ground plane leaf having a conductive element disposed thereupon in accordance with the present disclosure.

Yet another embodiment is described herein with reference to FIGS. 10, 10A, and 10B, wherein a microwave ablation probe 300 includes a ground plane assembly 320 having one or more deployable ground plane leaves 322 disposed in a radial arrangement to a dielectric distal end 306 of probe 300. Leaves 322 may be formed from resilient substrate material, e.g., shape memory alloy sheet material, shape memory polymeric sheet material, and/or resilient polymeric sheet material, such as without limitation, polyimide, e.g., Kapton™ film manufactured by E. I. du Pont de Nemours and Company of Wilmington, Del., United States. Leaves 322 may have a laminated construction, wherein in an embodiment, a substrate material may include a dielectric coating on an outer surface thereupon to form an insulating layer between a substrate material and tissue. In yet another embodiment illustrated in FIG. 13A, a leaf 360 may be formed from a non-metallic substrate 361, which may include one or more conductive elements 362 disposed thereupon having a substantially solid pattern. As seen in FIG. 13B, a leaf 370 may include one or more conductive elements 372 (e.g., circuit traces) arranged in a generally serpentine pattern, which may enhance or control ablation volumes. A contact region 363, 373 may additionally or alternatively be included to facilitate electrical and/or mechanical coupling of a leaf 360, 370 to an associated probe (e.g., a dielectric and/or outer conductor thereof). The disclosed conductive elements may provide a ground plane electrode and/or may be formed from resistance metal, e.g., nickel-chromium resistance metal (a.k.a. nichrome), through which an electric current may be passed. The electric current causes heating of the resistance metal which, in turn, causes heating of a shape memory substrate layer associated therewith, to activate shape memory material transformation to facilitate deployment of the ground plane electrode.

Figure 11:
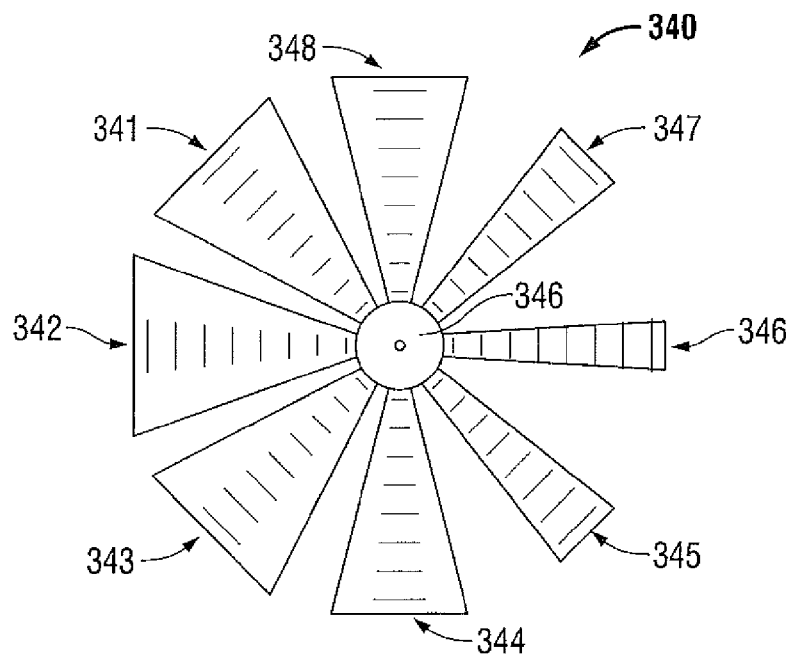
FIG. 11 is distal end view of a further embodiment of a microwave ablation probe having a deployable ground plane in accordance with the present disclosure.

In a further embodiment illustrated in FIG. 11, a ground plane assembly 340 includes one or more leaves 341-348 of varying shapes and/or sizes, which may improve or control an ablation pattern of a ground plane assembly and/or an associated probe, and which may tailor ablation performance to particular requirements of a surgical procedure.

Figure 12C:
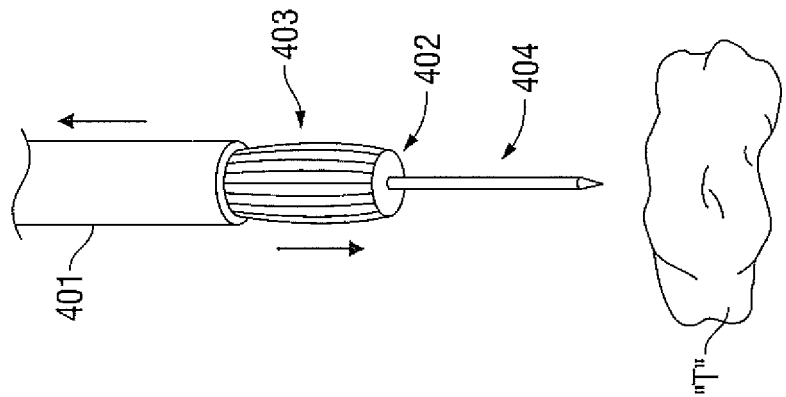
FIGS. 12A-12J illustrate a method of use of a microwave ablation probe having a deployable ground plane in accordance with the present disclosure.
Figure 12B:
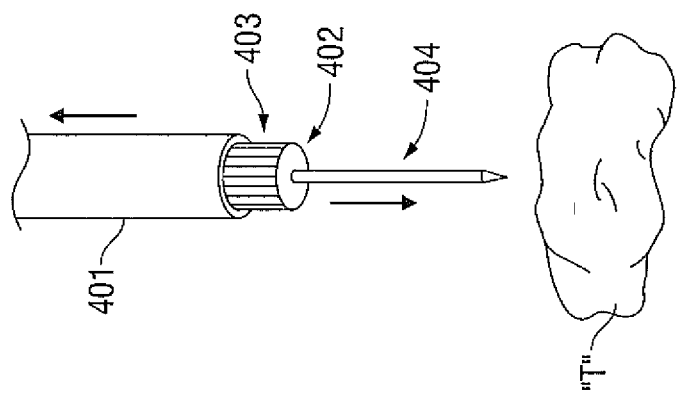
Figure 12A:
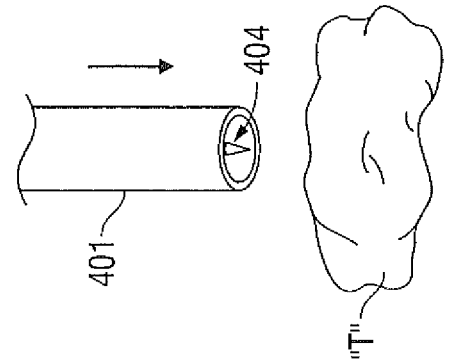
Figure 12F:
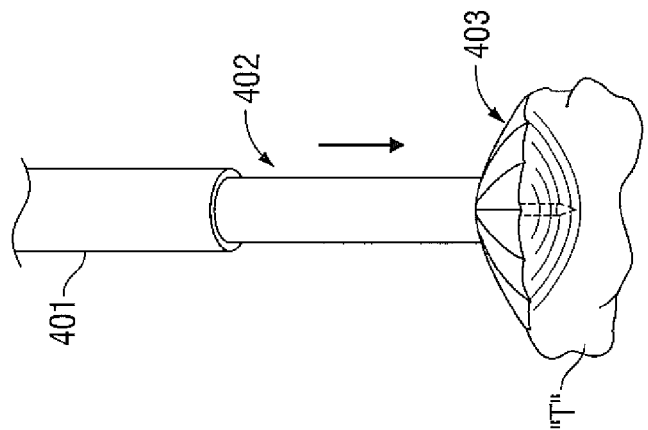
Figure 12E:
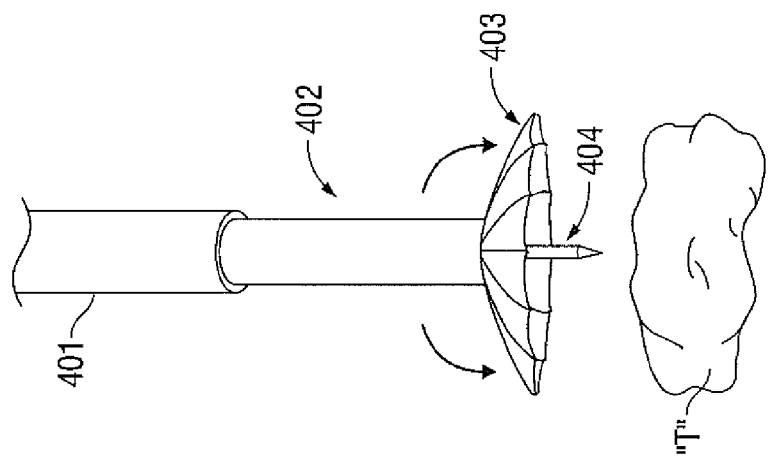
Figure 12D:
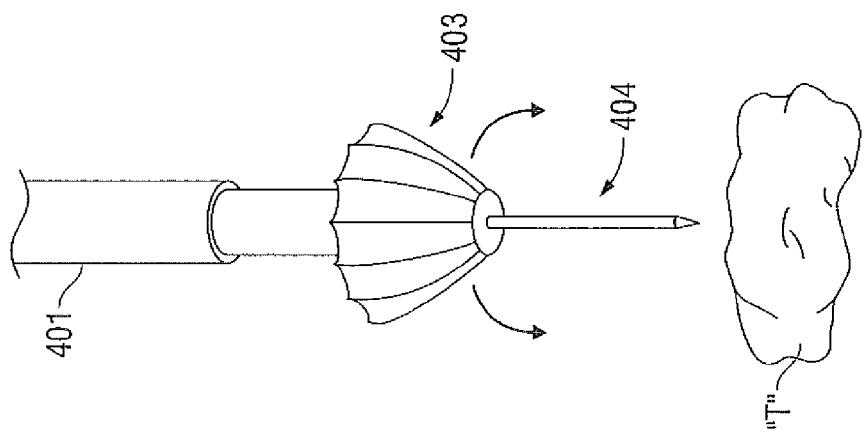

Turning now to FIGS. 12A-12J, a method of use of a microwave ablation probe having a deployable ground plane in accordance with the present disclosure is described. With reference to FIGS. 12A and 12B, the disclosed method includes the steps of providing to targeted tissue T at a surgical site a cannula 401 having stowed therein an ablation probe 402 that includes a deployable ground plane electrode 403 and a needle electrode 404. As seen in FIGS. 12B and 12C, the cannula 401 is retracted relative to the probe 402 to expose the deployable ground plane 403. Additionally or alternatively, the probe 402 may be advanced with respect to the cannula 401 and/or targeted tissue T. As the retraction of cannula 401 and/or the advancement of probe 402 proceeds, deployable ground plane 403 is exposed completely causing the deployment thereof into an open position as shown in FIGS. 12D and 12E.

Figure 12J:
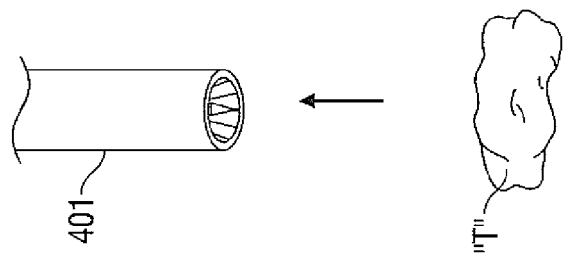
Figure 12I:
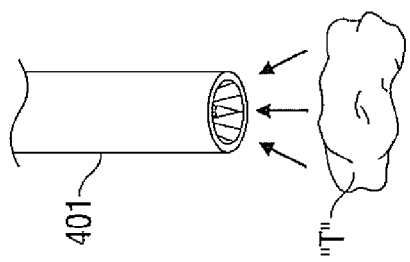
Figure 12H:
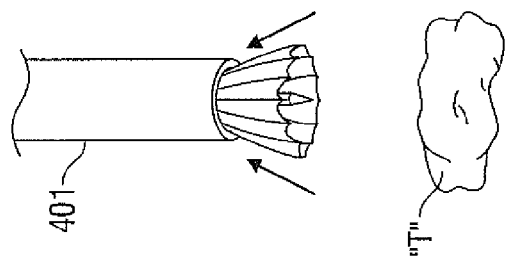
Figure 12G:
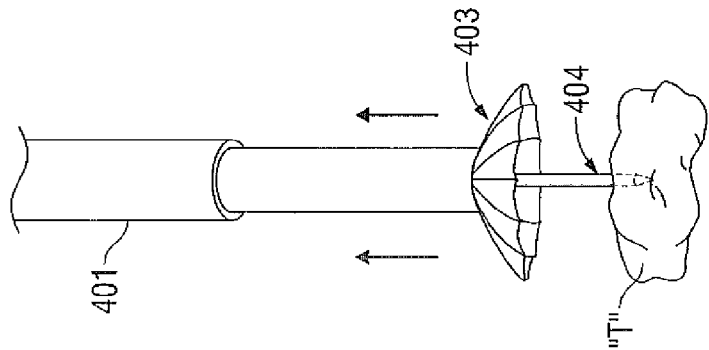

The probe 402, and optionally the cannula 401, are advanced toward the targeted tissue T thereby inserting needle electrode 404 into the targeted tissue and/or bringing ground plane 403 into contact with a surface thereof as shown in FIG. 12F. Electrosurgical energy may be applied via needle electrode 404 to facilitate the insertion thereof into targeted tissue T. Probe 402 is then energized to deliver ablation energy to tissue T via, e.g., needle electrode 404. The probe 402 is then retracted and needle electrode 404 removed from tissue T as shown in FIG. 12G. Probe 402 continues to be retracted into cannula 401, causing ground plane 403 to fold forward, and slide into cannula 401 as depicted in FIGS. 12H and 12I, Cannula 401 is then withdrawn from tissue T as shown in FIG. 12J.

It is envisioned the steps of the above method may be performed in a different order than that described, and/or the operations performed within an individual step or steps may be desirably be combined into a single step without departing from the scope and spirit of the method disclosed herein. For example, and without limitation, needle electrode 404 may be inserted into targeted tissue prior to deployment of ground plane 403, which may result in ground plane 403 to contact tissue T substantially immediately upon deployment. In another example, and without limitation, once probe 402 is retracted into cannula 401, causing ground plane 403 to fold forward, as depicted in FIGS. 12H, 12I, and 12J, subsequent retraction of cannula 401 relative to probe 402 results in the free end of ground plane 403 to be exposed from cannula 401 prior to the fixed end of ground plane 403.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A surgical ablation system, comprising:
   a source of ablation energy;
   a source of electrosurgical energy;
   a switching assembly configured to selectively and operably couple at least one of the source of ablation energy or the source of electrosurgical energy to an inner conductor of an ablation probe, the ablation probe including:
   a cannula having a proximal end and a distal end;
   a shaft slidably disposed within the cannula and having at least a stowed position and a deployed position;
   the inner conductor adapted to operably couple to the switching assembly, the inner conductor coaxially disposed within the shaft and extending from a distal end thereof to form a needle electrode; and
   a deployable ground plane electrode assembly coupled to the distal end of shaft, the deployable ground plane comprises a plurality of resilient wire elements circumferentially disposed about the distal end of the shaft and within the cannula when the shaft is in the stowed position,
   wherein the shaft is movable from the stowed position to the deployed position to extend the needle electrode and the deployable ground plane assembly past the distal end of the cannula thereby expanding the plurality of resilient wires radially from the distal end of the shaft.

2. The surgical ablation system in accordance with claim 1, wherein the shaft includes an outer conductor coaxially disposed on an outer surface thereof.

3. The surgical ablation system in accordance with claim 2, wherein the outer conductor is electrically coupled to the deployable ground plane electrode assembly.

4. The surgical ablation system in accordance with claim 1, wherein each of the plurality of the resilient wire elements includes a fixed end and a free end, wherein the fixed end thereof is fixed to the distal end of the shaft, and the deployable ground plane electrode assembly further includes a generally circular flexible ground plane membrane disposed upon each of the plurality of the resilient wire elements.

5. The surgical ablation system in accordance with claim 4, wherein each of the plurality of the resilient wire elements is configured to bias the ground plane membrane substantially radially from the shaft.

6. The surgical ablation system in accordance with claim 1, wherein each of the plurality of the resilient wire elements forms a loop having a first fixed end and a second fixed end, wherein the first fixed end and second fixed end thereof are fixed to the distal end of the shaft to form a generally semicircular loop, and the deployable ground plane electrode assembly further includes a flexible ground plane membrane disposed upon the generally semicircular loop.

7. The surgical ablation system in accordance with claim 1, wherein each of the plurality of the resilient wire elements is a resilient leaf element having a fixed end and a free end, wherein the fixed end thereof is fixed to the distal end of the shaft, and the deployable ground plane electrode assembly further includes a conductive element disposed on a surface of the resilient leaf element.

8. The surgical ablation system in accordance with claim 7, further comprising a dielectric coating disposed on the conductive element.

9. A surgical ablation probe, comprising:
   a cannula having a proximal end and a distal end;
   a shaft slidably disposed within the cannula and having at least a stowed position and a deployed position;
   an inner conductor coaxially disposed within the shaft and extending from a distal end thereof to form a needle electrode; and
   a deployable ground plane electrode assembly coupled to the distal end of shaft, the deployable ground plane comprises a plurality of resilient wire elements circumferentially disposed about the distal end of the shaft and within the cannula when the shaft is in the stowed position,
   wherein the shaft is movable from the stowed position to the deployed position to extend the needle electrode and the deployable ground plane assembly past the distal end of the cannula thereby expanding the plurality of resilient wires radially from the distal end of the shaft.

10. The surgical ablation probe in accordance with claim 9, wherein the shaft includes an outer conductor coaxially disposed on an outer surface thereof.

11. The surgical ablation probe in accordance with claim 10, wherein the outer conductor is electrically coupled to the deployable ground plane electrode assembly.

12. The surgical ablation probe in accordance with claim 9, wherein
    each of the plurality of the resilient wire elements includes a fixed end and a free end, wherein the fixed end thereof is fixed to the distal end of the shaft, and the deployable ground plane electrode assembly further includes a generally circular flexible ground plane membrane disposed upon each of the plurality of the resilient wire elements.

13. The surgical ablation probe in accordance with claim 12, wherein each of the plurality of the resilient wire elements is formed from material selected from the group consisting of shape memory alloy, nitinol, stainless steel, and platinum.

14. The surgical ablation probe in accordance with claim 12, wherein the flexible ground plane membrane is formed from material selected from the group consisting of metallic foil, metallic mesh, and metal-coated polymeric film.

15. The surgical ablation probe in accordance with claim 12, wherein the plurality of the resilient wire elements is configured to bias the ground plane membrane substantially radially from the shaft.

16. The surgical ablation probe in accordance with claim 9, wherein each of the plurality of the resilient wire elements forms a loop having a first fixed end and a second fixed end, wherein the first fixed end and second fixed end thereof are fixed to the distal end of the shaft to form a generally semicircular loop, and the deployable ground plane electrode assembly further includes a flexible ground plane membrane disposed upon the generally semicircular loop.

17. The surgical ablation probe in accordance with claim 9, wherein each of the plurality of the resilient wire elements forms a resilient leaf element having a fixed end and a free end, wherein the fixed end thereof is fixed to the distal end of the shaft, and the deployable ground plane electrode assembly further includes a conductive element disposed on a surface of the resilient leaf element.

18. The surgical ablation probe in accordance with claim 17, further comprising a dielectric coating disposed on the conductive element.

19. The surgical ablation probe in accordance with claim 17, wherein each of the plurality of the resilient wire elements is formed from material selected from the group consisting of metal, polymeric material, shape memory metal, shape memory polymeric material, and polyimide.

20. A method of using a surgical ablation system, comprising:

positioning an ablation probe at an operative site, wherein the ablation probe includes a cannula having a shaft slidably disposed therein with a deployable ground plane electrode assembly coupled to a distal end of the shaft and a needle electrode extending from the distal end of the shaft, the deployable ground plane electrode assembly comprising a plurality of resilient wire elements circumferentially disposed about the distal end of the shaft;

deploying the shaft to extend the deployable ground plane assembly and the needle electrode past the distal end of the cannula thereby expanding the plurality of resilient wires radially from the distal end of the shaft;

delivering electrosurgical energy to tissue via the needle electrode to facilitate the insertion of the needle electrode into tissue;

inserting the needle electrode into tissue;

delivering ablation energy to tissue via the needle electrode;

withdrawing the needle electrode from tissue;

retracting the ground plane electrode assembly into the cannula; and removing the ablation probe from the operative site.

* * * * *